US010208264B1

(12) United States Patent
Wright et al.

(10) Patent No.: US 10,208,264 B1
(45) Date of Patent: Feb. 19, 2019

(54) HYBRID METALLIZED ORGANIC FUELS

(71) Applicant: The United States of America, as represented by the Secretary of the Navy, Washington, DC (US)

(72) Inventors: Michael E. Wright, Ridgecrest, CA (US); Kelvin T. Higa, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/723,689

(22) Filed: Oct. 3, 2017

Related U.S. Application Data

(62) Division of application No. 14/674,378, filed on Mar. 31, 2015, now Pat. No. 9,822,320.

(51) Int. Cl.
*C10L 1/12* (2006.01)
*C07C 2/50* (2006.01)
(Continued)

(52) U.S. Cl.
CPC ............... *C10L 1/12* (2013.01); *C06B 45/32* (2013.01); *C07C 2/50* (2013.01); *C07C 5/22* (2013.01); *C07C 13/68* (2013.01); *C07F 5/027* (2013.01); *C07F 7/0805* (2013.01); *C10L 1/18* (2013.01); *C10L 1/28* (2013.01); *C10L 1/30* (2013.01); *C07C 2603/86* (2017.05); *C10L 1/1208* (2013.01); *C10L 1/1608* (2013.01); *C10L 1/303* (2013.01); *C10L 2200/0204* (2013.01); *C10L 2200/0254* (2013.01); *C10L 2200/0272* (2013.01); *C10L 2230/22* (2013.01); *C10L 2250/06* (2013.01); *C10L 2270/04* (2013.01); *C10L 2290/20* (2013.01); *C10L 2290/24* (2013.01)

(58) Field of Classification Search
CPC combination set(s) only.
See application file for complete search history.

(56) References Cited

U.S. PATENT DOCUMENTS 5,076,813 A * 12/1991 Alberici ............... C10L 1/04
44/300
5,616,882 A 4/1997 Nichols et al.
(Continued)

OTHER PUBLICATIONS

Jones, et al. Experimental study of combustion charasteristics of nanoscale metal and metal oxide additives in biofuels, Nano. Res. Let. 2001, 6:246 1.

*Primary Examiner* — Ellen M McAvoy
*Assistant Examiner* — Chantel L Graham
(74) *Attorney, Agent, or Firm* — Charlene A. Haley

(57) ABSTRACT

A formulation and methods for making high energy organic fuels that incorporate suspended metal particles with metal particle sized ranging from 33 nm to 5 micron. The hybrid organic fuels contain superior density and/or energy content to conventional liquid organic fuels. These hybrid organic fuels used in combination with metal particle afford fuels with 5 to 80% more net heat of combustion (based on volume). These fuels should extend the distant range for jets, liquid rocket engines, SCRAM jet engines, and improve energy content in fuel-air explosive applications such as fuel-air explosives and in the Multi-Effects Weapons System (MEWS) where the fuel is used both for propulsion and explosive effects.

4 Claims, 4 Drawing Sheets

(51) Int. Cl.
*C10L 1/28* (2006.01)
*C10L 1/30* (2006.01)
*C10L 1/18* (2006.01)
*C07C 5/22* (2006.01)
*C07C 13/68* (2006.01)
*C07F 7/08* (2006.01)
*C07F 5/02* (2006.01)
*C06B 45/32* (2006.01)
*C10L 1/16* (2006.01)

(56) References Cited

U.S. PATENT DOCUMENTS

2003/0072250 A1* 4/2003 Dinnocenzo ........... G11B 7/244
 369/275.1
2009/0000186 A1 1/2009 Sanders et al.

* cited by examiner

HYBRID METALLIZED ORGANIC FUELS

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention relates to for preparing a novel class of high energy fuels capable of providing a significant increase in range for vehicles having volume limited fuel storage.

Figure 1:
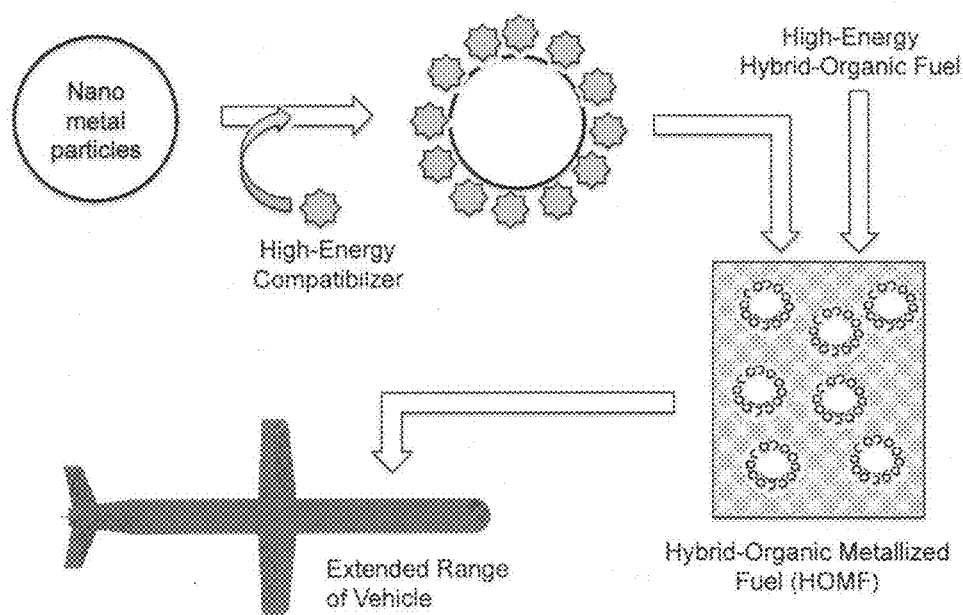
FIG. 1 is a high level block diagram illustrating the process of how the hybrid metallized organic fuels are manufactured, according to embodiment of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to for preparing a novel class of high energy fuels capable of providing a significant increase in range for vehicles having volume limited fuel storage. Creating new high energy fuels is critical to creating long endurance propulsion for volume limited vehicles that can include underwater, hypersonic, and normal land/sea/air vehicles and missions.

Organic fuels are used to suspend modified nano-sized metal particles (nanometals) in such a manner that they can be utilized in several motor types that include, but not limited to, turbine, rocket propulsion, ignition combustion, and compression ignition engines. New art is presented that creates hybrid-organic fuels that contain superior density and/or energy content themselves. These hybrid organic fuels used in combination with nanometals to afford fuels with 5 to 80% more net heat of combustion (based on volume). Thus, embodiments of this invention present a method for 1) creating new high-energy/high-density fuels, 2) modifying nanometals to create a stable suspension and mitigate aggregation of the nano metal particles, and 3) utilization of these metalized hybrid organic fuels to improve motor/engine performance in terms of range and combustion characteristics. A further potential application of the hybrid metallized organic fuels is for the Multi-Effects Weapons System (MEWS) where the fuel is used both for propulsion and explosive effects. Hybrid metallized organic fuels also have potential use for Enhanced Blast/Volumetric weapons.

Some embodiments of the invention provide at least one fuel that provides a significant energy increase to "liquid" fuels currently used in certain engine and motor applications, hence, the invention fuel performance characteristics are far superior to what can be obtained using strictly organic fuels. Embodiments of the invention are particularly useful and powerful in situations where the fuel volume is restricted due to mission requirements.

Metallized fuels have been explored in the area of solid rocket propulsion. Patent work reported by Reed et al. from China Lake demonstrated the use of nanoaluminum in propellant systems using polymeric binders and various oxidizers (such potassium perchlorate). U.S. Pat. No. 6,454,886 also teaches the art of preparing solid mixtures of metallic particles within a solid oxidizer for use in solid rocket motors.

In the masters' thesis of M. Jones (University of Toledo, 2011) entitled, "Ignition and Combustion Characteristics of Nanoscale Metal and Metal Oxide Additives in Biofuel (ethanol) and Hydrocarbons" reported data consistent with excess energy output from metalized fuels; however, at very low loadings of nanoaluminum. The authors did not present data on high density or high-energy fuels such as JP-10 and similar, or quadricyclane based fuels, nor did they explore the possibility of high metal loadings near those used in embodiments of the invention.

Work has been reported that surface modification of nanometals does greatly increase the ability to "solubilize" the particles [R. J. Jouet et al. *Chem. Mater.* 2005, 17(11), 2987-2996 and M. Cokoja et al. *Chem. Mater.* 2007, 19(23), 5721-5733]

A very general description for the some of the invention embodiments is shown in FIG. 1. Using known art the metal nanoparticles are generated and then delivered to apparatus and contacted with surface modifiers described in the embodiments of this invention. The now modified and stabilized metal nanoparticles are placed and mixed with an organic fuel, some of which are embodiments of the present invention, and finally the Hybrid Metallized Organic Fuel (HMOF) can be used in rocket, diesel, turbine, or scram jet applications when combined with at least one liquid, gas, or solid oxidizer.

New fuels are invented by combining/joining organic molecules that include chemical structural features that may have multiple rings with or without ring-strain in such a manner to create novel organic fuels that possess high-energy, high density, and have good to excellent low temperature physical characteristics. For example, in some embodiments the invention fuels have excellent low temperature viscosities (e.g. less than 8.5 cSt) below −20° C. The latter is critical for use in applications at high altitudes where low temperatures are often encountered. In some embodiments the organic fuels of the invention will include ring-strain that impart high-energy to the fuel both on a volumetric and gravimetric basis. Some embodiments of the invention describe synthetic methods to create fuels with at least one organic moiety having ring strain. In other embodiments, synthetic methods are provided to prepare organic fuels that have at least two organic moieties per fuel molecule that have ring strain.

Figure 2:
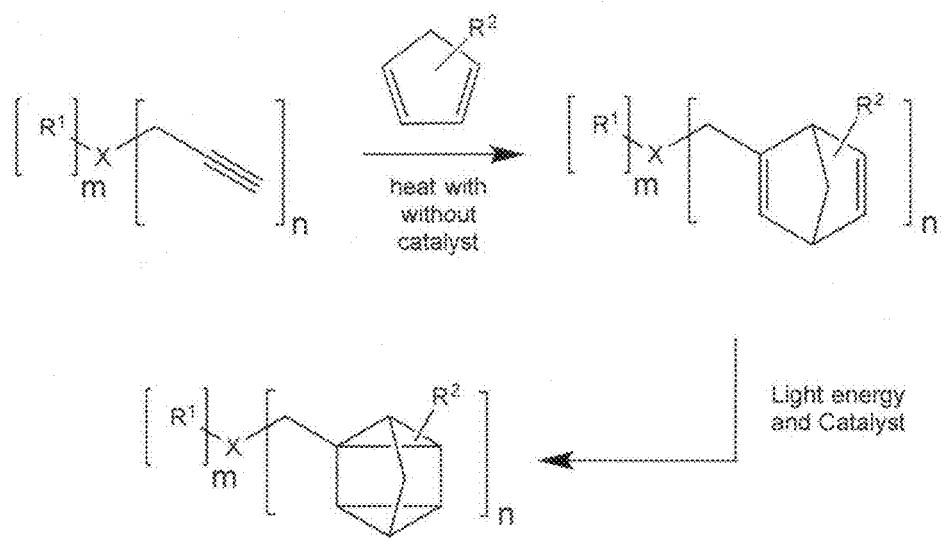
FIG. 2 is a synthesis diagram for preparing dendrimeric hybrid-organic fuel, according to embodiments of the invention.

In FIG. 2, a general synthetic scheme is shown for preparing invention organic fuels that have at least one organic moiety having ring strain. By tethering, or it can be said linking the ring-strained moieties together, the invention fuels provide additional energy density to the fuel not possible with existing fuels and thus provide energy density superior to existing organic fuels know in the art. Utilizing silicon (X=Si) as a linker atom enables superior low temperature performance of the high-density high-energy organic fuels.

In FIG. 2, X can be carbon, silicon, or a boron atom or any combination of the elements. In some embodiments, the X atom can also be selected from a Group 3 or Group 4 element or a combination of the two. In the case of X is carbon or silicon, then (n+m)=4; hence when n=2 then m=2. For each element used as X in embodiments of the invention, the total number (i.e. m+n) is equal to the number required create a neutral molecule (i.e. no net charge on X). The substituent $R^1$ is an alkyl group having one to twenty carbon atoms. In some embodiments the $R^1$ is a linear carbon chain and others have at least one branch point. In other embodiments the $R^1$ group is an alkoxy group, for example MeO. Alkoxy groups can be used in combination with alkyl groups as embodiments of the invention. For the diene component, $R^2$ may be hydrogen or a carbon group of 1 to 20 carbons or any mixture of the two. In some embodiments a mixture of cyclopentadiene ($R^2$=H) and methylcyclopentadiene ($R^2$=methyl) is used as the diene reactive component.

In FIG. 2, the diene can be reacted with acetylenic core using heat to accelerate the reaction. In some embodiments, a catalyst may be employed to accelerate the reaction between the diene and acetylenic core group. For example, Lewis acid catalysts are known to accelerate Diels-Alder reactions. One example of a Lewis acid catalyst is aluminum trichloride.

In organic chemistry, ring strain is a type of instability that exists when bonds in a molecule form angles that are abnormal. Strain is most commonly discussed for small rings, such as cyclopropanes and cyclobutanes where the C—C—C angles deviate substantially from the idealized values of approximately 109°. Because of their high strain, the heat of combustion for these small rings is elevated. Ring strain results from a combination of angle strain, conformational strain or Pitzer strain, and transannular strain or van der Waals strain. The simplest examples of angle strain are small cycloalkanes such as cyclopropane and cyclobutane. Cyclic alkenes are subject to strain resulting from distortion of the sp$^2$-hybridized carbon centers. Illustrative is $C_{60}$ where the carbon centres are pyramidalized. This distortion enhances the reactivity of this molecule. Angle strain also is the basis of Bredt's rule which dictates that bridgehead carbon centers are not incorporated in alkenes because the resulting alkene would be subject to extreme angle strain. (Smith, Michael B.; March, Jerry (2007), Advanced Organic Chemistry: Reactions, Mechanisms, and Structure (6th ed.), New York: Wiley-Interscience, ISBN 0-471-72091-7 and see: Wiberg, K. (1986) in "The Concept of Strain in Organic Chemistry" *Angew. Chem. In. Ed Engl.* 25 (4): 312-322).

The following reaction illustrates a method to rapidly connect high-density molecules to create a mixed dendrimer-like high density fuel:

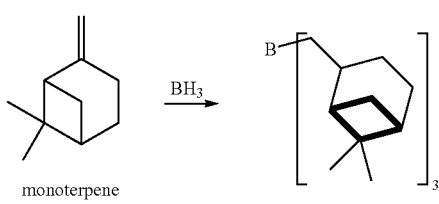

The organoborane can be RBH$_2$ where R is a carbon chain having one to twenty carbons and may contain zero or at one branched carbon, in this embodiment two monoterpenes would react to form the hybrid organic fuel. The bolded bonds in the product are to help identify the cyclobutane ring that creates ring strain and that in turn brings additional energy output upon combustion.

In embodiments, an olefin, like fulvene can be reacted with silane reagent having at least one hydrogen atom to form an intermediate diene that can further be converted to a quadricyclane derivative after reaction with acetylene and then catalytic conversion (using light (hv)) to the final hybrid quadricyclane based high-energy and high-density fuel:

The organosilane includes at least one hydrogen atom necessary for the

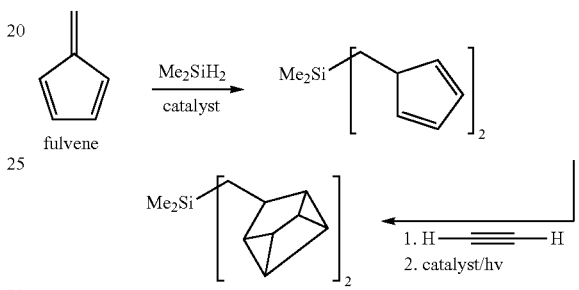

hydrosilylation reaction. In embodiments, the organosilane reagent has one or more alkyl groups having one to twenty carbons and any combination thereof.

In embodiments of the invention high-energy fuels can be prepared by reacting cyclopentadiene or derivatives thereof with dienes, and then converted to the bis(quadricyclanes):

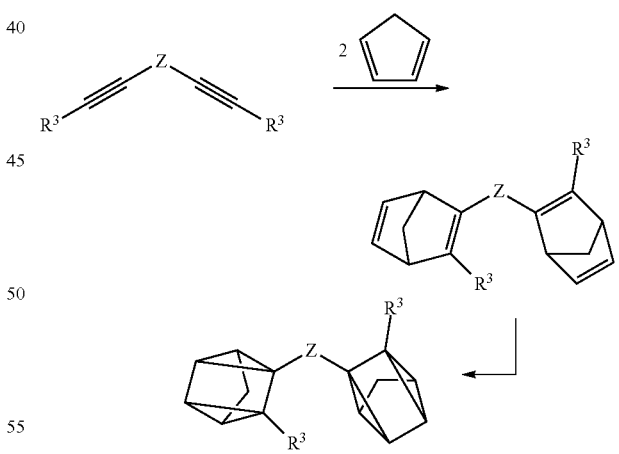

The Z group can be nil (i.e. rings directly attached, no spacer) or Z can be a hydrocarbon chain from 1 to 20 carbons that can be linear or have one or more branch points (e.g. —CH$_2$CH(CH$_3$)CH$_2$—). The R$^3$ substituent can be hydrogen or an alkyl group of one to twenty carbons or any combination thereof. These invention fuels made with this formula can be added to other fuels including quadricyclane, JP-5, JP-10, or RP-1 to create diesel, turbine, and rocket fuels with greater energy density on a volume basis. The new high-energy fuels of embodiments of the invention can be blended with normal jet or diesel or rocket fuels at levels from 1% to 99% by weight to create a second fuel that have additional combustion energy per unit volume.

The organic feed can be selected from petroleum and/or bio-organic molecules. The bio-organics can be selected from monoterpenes, sesquiterpenes, and diterpenes and other biosynthesized molecules that contain at least one alkene functional group. Borane ($BH_3$) and other borane molecules may be used in embodiments of the invention that include at least one B—H group and then any combination of alkyl or aromatic substituents. These represent a novel class of high-density and high-energy hybrid-organic fuels that are ideally suited for combining with nanometals or sometimes referred to as metal nano-particles herein.

Metal nanoparticles have been prepared that are surface modified to promote suspension within the hybrid organic fuel and mitigate aggregation of the nanometals in the fuel over periods of storage. It is known to those experienced in the art that nano aluminum powders (33 nm, 50 nm 80 nm, or any combination thereof) can be been coated with a monolayer of long chain aliphatic acids, for example palmitic acid or stearic acid or with perfluoroacids including perfluoro nonadecanoic acid, and these modified particles show less tendency to aggregate and hence remain dispersed in solution. The organic acid chain length and side groups used to coat the metal powders will have some affect on the ability to modify suspended metal powder interactions and thus control suspension properties; however, this is unique for each type of modification and particle size and is not well understood. The metal particle (coated with an acid) solubility in a given solvent is controlled by the organic acid properties. As the organic acid is modified to be more similar to the solvent, the solubility of the modified metal particle increases. This is how surfactants work in detergents. The hydrophobic ends of the surfactant form micelles around organic liquids exposing the hydrophilic ends making the micelles soluble in water.

In embodiments, the suspension properties of small micron size aluminum (e.g. 2-10 micron) powders is enhanced with organic acid coatings that provide an increase in dispersion properties and also impart a feature of that in providing significant strain-energy that in turn provides additional combustion output:

In embodiments, the surface modifying groups are prepared as shown:

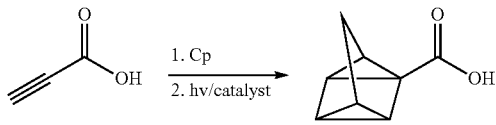

The cyclopentadiene (Cp) is treated with propionic acid to create the norbornadiene carboxylic acid (not shown) that is converted to the carboxy-quadricyclane using light and a metal catalyst. In embodiments, at least one copper catalyst is utilized to make the quadricyclane structure. Other catalysts are known to those experienced in the art of electrocyclic ring closure reactions and are suitable for the above reaction as well. In other embodiments the starting acetylenic carboxylic acid materials have the formula: HC≡C—$(CH_2)_nCO_2H$ where n is an integer from 1 to 20. In embodiments, the alkyl chain between the acetylene group and the carboxy group has at least one branch point with a methyl group or larger (e.g. C1 to C6).

In embodiments, the compatibilizing agent has a silicon or boron element with at least one leaving group that can react with any metal oxide on the surface of the nano metal particles. In embodiments, there is less introduction of oxidized carbon or silicon or boron, hence, provides an even further increase in the fuels energy output upon oxidation of the inventions compatibilized (i.e. surface modified) metal nano particles.

Figure 3:
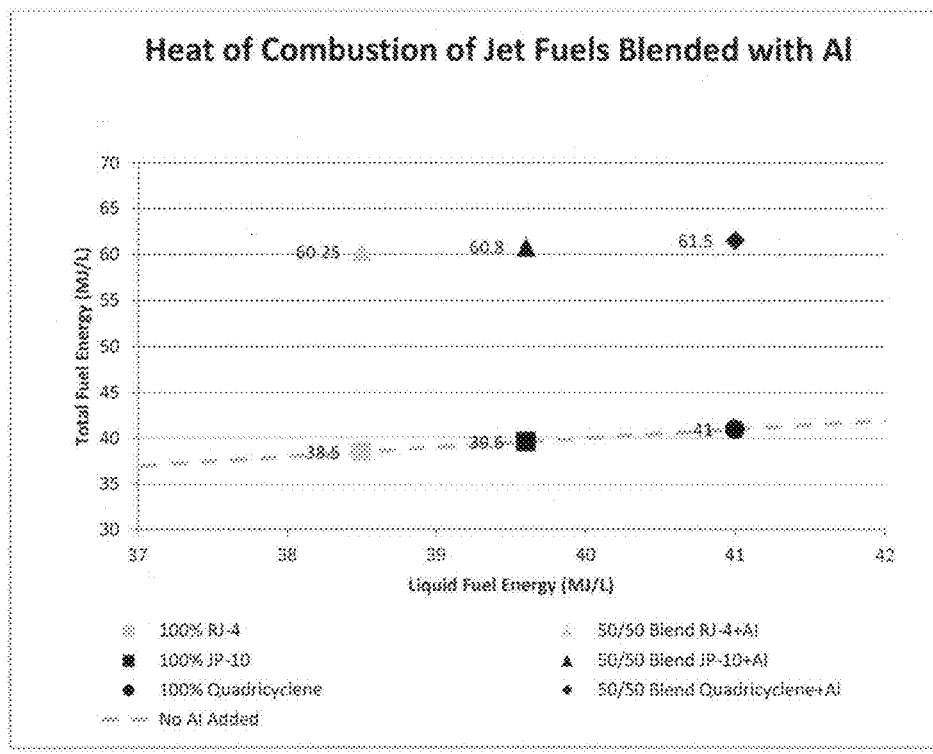
FIG. 3 is a plot showing the increase in energy for hybrid metallized organic fuel (HMOF), according to embodiments of the invention.
Figure 4:
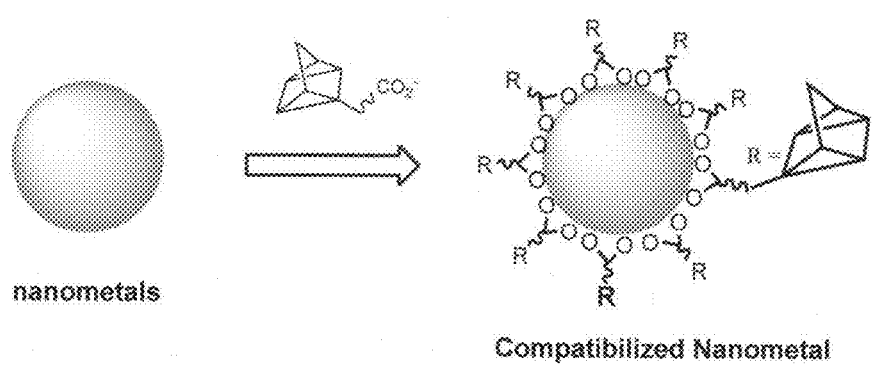
FIG. 4 is a chemical schematic showing the conversion of nanometals into a compatibilized nanometal, according to embodiments of the invention.

In embodiments of the invention, organic fuels are combined with nanometals (and/or small micron metal powders) to produce "Hybrid Metalized Organic Fuels (HMOF)" which have far superior combustion energies on a volumetric basis than any current existing "liquid" fuel that can be used create power or thrust. This process can utilize standard high-density fuels, like JP-10 or other rocket fuels (RP-1), but is best when used in combination with the organic and hybrid fuels created in this invention. A plot of the increase in net combustion energy is given in FIG. 3 is to show typical existing hydrocarbon fuels. In embodiments, the compatibilized metal nanoparticles can be used with conventional hydrocarbon fuels and provide an increase in combustion output (wt to wt of metal used in the fuel). Thus, the fuel performance is greater than the values plotted in FIG. 3 for the same weight fraction of nano metal added (based on wt of metal) while providing the additional benefit of providing a stable dispersion of invention metal nanoparticles within the fuel sample.

FIG. 3 illustrates the increase in combustion energy for a 50-50 wt-% blend of nanoaluminum as a function of organic fuel energy content and assumes all the metal is aluminum, not aluminum oxide. Stability of the aluminum surface is critical to maintaining the increase in combustion energy. This is especially true for smaller aluminum particles where oxide formation on the surface can lead to large drop in the wt-% of pure aluminum contained in the nanoparticle. In embodiments, the high-energy compatiblizing agents enhance the aluminum surface stability towards oxidation while providing the additional and unprecedented benefit in increased fuel performance due to the invention modifiers containing ring-strain energy.

Mild increases in energy content can be made by increasing the density/energy content of pure organic fuels as seen in going from JP-5 to JP-10; however, the plot in FIG. 3 nicely illustrates that for a large increase in performance for volume restricted applications. HMOF's can provide a true performance solution that can 1) easily provide a 50% increase in energy output during combustion, 2) provide increased dispersion of the nanometals, and 3) deliver a further increase in energy output by having ring-strain as a structural part of the chemically modified surface layer. Since small particles have a large surface area, embodiments of the invention play a greater role for enhancing a net combustion output gain over BOTH organic fuels and those compatibilized with nanometals employing traditional modifiers (e.g. stearic acid).

The U.S. Military use a different classification system of JP (for "Jet Propellant") numbers (e.g. JP-1 through JP-10). Jet fuels, also called turbine fuels, can be classified as kerosene or naphtha-type. JP-5 is a yellow kerosene-based jet fuel and is a complex mixture of hydrocarbons, containing alkanes, naphthenes, and aromatic hydrocarbons that weighs 6.8 pounds per U.S. gallon (0.81 kg/L), and is fractionated during processing to have a high flash point (min. 60° C. or 140° F.) and a freezing point of −46° C. (−51° F.). JP-10 is a high density and specialized turbine fuel for missiles and includes a mixture of (in decreasing order) endo-tetrahydrodicyclopentadiene, exo-tetrahydrodicyclopentadiene, and adamantane and achieves a lower low-temperature service limit of −65° F. (−54° C.).

Example 1

Under an inert and purified nitrogen atmosphere a 0.01 M toluene (100 mL) solution including carboxy quadricyclane is placed in contact with 10 g of nanoaluminum (10 micron) with stirring for a period of 1 h under a purified atmosphere of nitrogen. The modified nano-metal particles are isolated by centrifugation, washed with 20 mL of fresh toluene, and then isolated again and dried to afford ~9 to 10 g of surface modified invention nanoaluminum particles.

Prophetic examples are for illustration purposes only and not to be used to limit any of the embodiments.

Embodiments of the invention generally relate to methods for producing quadricyclanes including, providing at least one multifunctionalized acetylenic core having at least one to four arms,

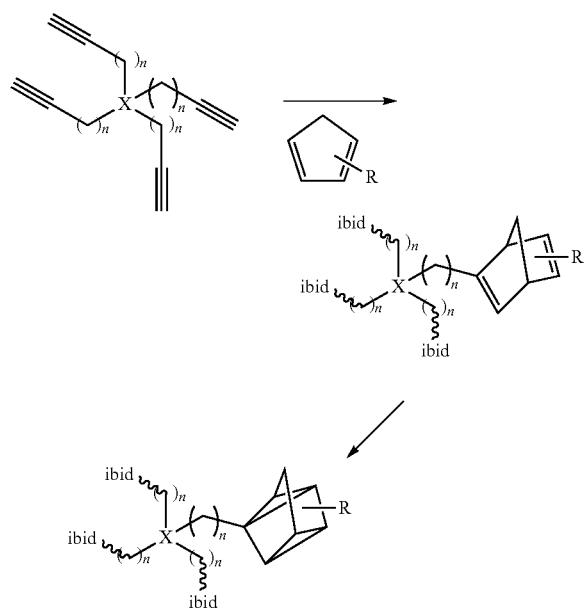

where n is an integer from 1 to 10 or 1-21 and where each arm is replaced with a hydrogen or suitable alkyl or aromatic group, X is selected from the group consisting of carbon, silicon, boron, or any combination thereof, R is selected from the group consisting of an alkyl (C1 to C8 methyl to octyl), and where at least one multifunctionalized acetylenic core is reacted with conjugated dienes or any composition having at least one ring strain molecule and subjected to light and at least one fixed bed catalyst to produce quadricyclanes having ring strain-molecules. Bio-organics can be selected from monoterpenes, sesquiterpenes, and diterpenes and other biosynthesized molecules including at least one alkene functional group. In embodiments, light can be white light or UV light which drives the reaction.

Another aspect of the invention generally relates to methods for making hybrid metallized organic fuels including, coating metal nanoparticles with a monolayer of long chain aliphatic acids or with perfluoroacid to produce modified metal nanoparticles for enhanced particle dispersion or coating with metal nanoparticles with quadricyclanes having ring strain-molecules, where the quadricyclanes have at least one multifunctionalized acetylenic core having at least one to four arms,

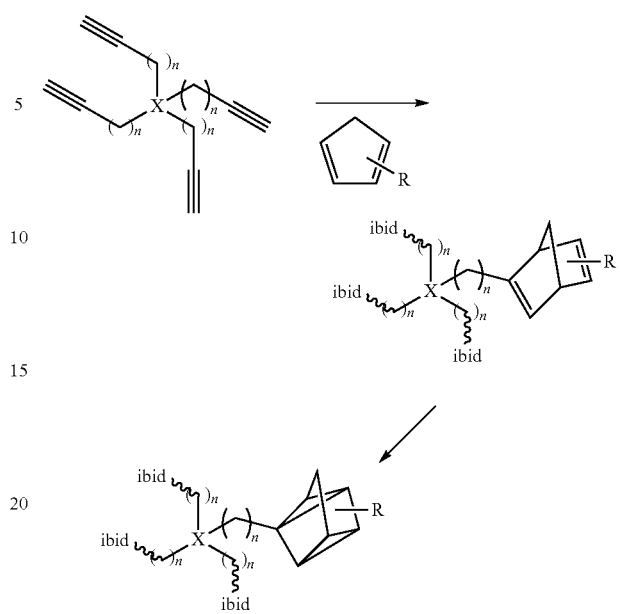

where the quadricyclanes include n is an integer from 1 to 21 and where each arm is replaced with a hydrogen or suitable alkyl or aromatic group, X is selected from the group consisting of carbon, silicon, boron, or any combination thereof, R is selected from the group consisting of an alkyl (C1 to C8 methyl to octyl), and where at least one multifunctionalized acetylenic core is reacted with conjugated dienes or any composition having at least one ring strain molecule and subjected to light and at least one fixed bed catalyst to produce quadricyclanes having ring strain-molecules.

In embodiments, X is selected from the group consisting of borane ($BH_3$) or other borane based molecules having at least one B—H group and any combination of alkyl or aromatic substituents. In other embodiments, X is silicon including one to four hydrogens and any combinations of alkyl or aromatic substituents. In embodiments, the long chain aliphatic acids are selected from the group consisting of palmitic acid, stearic acid, long chained organic acids, branched chained acids, $C_7H_{15}CO_2H$ to $C_{21}H_{43}CO_2H$ Diacids, and $HO_2C-(CH_2)nCO_2H$, wherein said n=7 to 21. In embodiments, the metal nanoparticles are selected from the group consisting of aluminum particles or powders, nano boron, and nano Ti. In other embodiments, the metal nanoparticles having a particle size in the range from about 30 to about 99 nm. Yet in other embodiments, the metal particles are aluminum having a particle size ranging from about 0.1 to about 5 microns.

In embodiments, hybrid metallized organic fuels have a 50-50 wt-% blend of nanoaluminum. In embodiments, at least about 80% to about 99% of the surface of the modified metal nanoparticles are coated with quadricyclanes having ring strain-molecules. In embodiments, at least one perfluoroacid is selected from the group consisting of perflouro nonadecanoic acid and $C_7F_{15}CO_2H$ to $C_{21}F_{43}CO_2H$. In embodiments, the hybrid metallized organic fuels are blended with JP-5 and/or JP-10. In embodiments, JP-5 or JP-10 have a blend of about 0.1% by weight percentage to about 50 by weight percentage. In embodiments, the hybrid metallized organic fuels are blended with JP-5 and/or JP-10 having a heat of combustion of total fuel energy ranging from about 60 MJ/L to about 62 MJ/L.

Other aspects of the invention generally relate to the products made by the above methods including hybrid metallized organic fuels, quadricyclanes, and hybrid metallized organic fuel blends with JP-5 and/or JP-10.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A hybrid metallized organic fuel, comprising:
   at least one multifunctionalized acetylenic core having at least one to four arms,

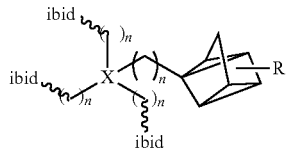

n is an integer from 1 to 21 and wherein each said arm is replaced with a hydrogen or suitable alkyl or aromatic group;
   X is selected from the group consisting of carbon, silicon, boron, or any combination thereof;
   R is selected from the group consisting of an alkyl (C1 to C8 methyl to octyl); and
   nanoaluminum present in an amount of about 50 wt % based on a total wt % of the hybrid metallized organic fuel.

2. A hybrid metallized organic fuel blend, comprising:
   at least one multifunctionalized acetylenic core having at least one to four arms,

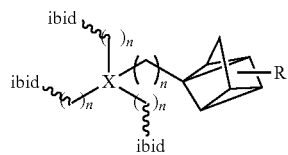

n is an integer from 1 to 21 and wherein each said arm is replaced with a hydrogen or suitable alkyl or aromatic group;
   X is selected from the group consisting of carbon, silicon, boron, or any combination thereof;
   R is selected from the group consisting of an alkyl (C1 to C8 methyl to octyl); and
   at least one of JP-5 and JP-10 fuel.

3. The hybrid metallized organic fuel blend according to claim 2, wherein at least one of said JP-5 or JP-10 is a blend present in an amount ranging from about 0.1 wt % to about 50 wt % based on a total wt % of the hybrid metallized organic fuel blend.

4. The hybrid metallized organic fuel blend according to claim 2, wherein said hybrid metallized organic fuel blend is blended with at least one of JP-5 and JP-10 having a heat of combustion of total fuel energy ranging from about 60 MJ/L to about 62 MJ/L.

* * * * *